United States Patent
Scecina et al.

(10) Patent No.: US 6,615,151 B1
(45) Date of Patent: Sep. 2, 2003

(54) METHOD FOR CREATING SPECTRAL INSTRUMENT VARIATION TOLERANCE IN CALIBRATION ALGORITHMS

(75) Inventors: Thomas Scecina, Medfield, MA (US); Theodore E. Cadell, Conestogo (CA); Romuald Pawluczyk, Conestogo (CA)

(73) Assignee: CME Telemetrix Inc., Waterloo (CA)

( * ) Notice: Subject to any disclaimer, the term of this patent is extended or adjusted under 35 U.S.C. 154(b) by 0 days.

(21) Appl. No.: 09/939,707

(22) Filed: Aug. 28, 2001

Related U.S. Application Data

(60) Provisional application No. 60/228,119, filed on Aug. 28, 2000.

(51) Int. Cl.$^7$ .......................... G01N 15/06; G06F 15/20
(52) U.S. Cl. .......................... 702/85; 250/573; 702/90; 703/2
(58) Field of Search .......................... 702/28, 85, 86, 702/90, 127; 703/2; 250/573; 600/322; 700/110

(56) References Cited

U.S. PATENT DOCUMENTS

| | | | | |
|---|---|---|---|---|
| 5,243,546 A | * | 9/1993 | Maggard | 702/90 |
| 5,361,758 A | | 11/1994 | Hall et al. | 600/322 |
| 5,459,677 A | * | 10/1995 | Kowalski et al. | 703/2 |
| 6,441,388 B1 | * | 8/2002 | Thomas et al. | 250/573 |

OTHER PUBLICATIONS

E. Bouverese et al., "Calibration transfer across near–infrared spectometric instruments using Shenk's algorithm: effects of different standardisation samples," *Analytica Chimica Acta* (1994), 297:405–416, Elsevier Science B.V.
F. Despagne et al., "Intersite transfer of industrial calibration models," *Analytica Chimica Acta*, (2000), 406:223–245, Elsevier Science B.V.
D.M. Haaland, "Synthetic Multivariate Models to Accommodate Unmodeled Interfering Spectral Components during Quantitative Spectral Analyses," *Applied Spectroscopy* (2000) 54(3):246–254. Society for Applied Spectroscopy.
D. Ozdemir et al., "Hybrid Calibration Models: An Alternative to Calibration Transfer," *Applied Spectroscopy* (1998) 52(4):599–603, Society for Applied Spectroscopy.
G.W. Small, "Data Handling Issues for Near–Infrared Glucose Measurements," http://www.ieee.org/organizatoins/pubs/newsletters/leos/apr98/datahandling.htm.
Y. Wang et al., "Multivariate Instrument Standardization," *Analytical Chemistry* 1991, 63(23):2750–2756.
R.W. Waynant et al., "Overview of Non–Invasive Fluid Glucose Measurement Using Optical Techniques to Maintain Glucose Control in Diabetes Mellitus," *Leos Newsletter*, Apr. 1998 (Special Issue), pp. 3–9.

\* cited by examiner

*Primary Examiner*—John Barlow
*Assistant Examiner*—John Le
(74) *Attorney, Agent, or Firm*—Foley & Lardner

(57) ABSTRACT

The present invention relates to a method of building instrument variation tolerance into calibration algorithms for spectroscopic devices for chemical composition analysis with spectroscopic methods. The method of the present invention is particularly suitable for blood glucose, cholesterol and other chemical components prediction based on near-infrared spectrophotometry measurements. A method includes developing a calibration algorithm on a first instrument; applying the calibration algorithm to a second instrument; calibrating the second instrument and adjusting the calibration algorithm to account for differences between the first instrument and the second instrument; and repeating the step of applying (above) in respect of (n) further instruments to provide a calibration algorithm which may then be used on other instruments. Methods are also provided that develop calibration algorithms by adding instrument variations, based on mathematical manipulation, of the spectral data collected on calibration instruments.

2 Claims, No Drawings

METHOD FOR CREATING SPECTRAL INSTRUMENT VARIATION TOLERANCE IN CALIBRATION ALGORITHMS

This application claims priority from U.S. provisional application Ser. No. 60/228,119, filed Aug. 28, 2000, the contents of which are herein incorporated by reference.

FIELD OF THE INVENTION

The present invention relates to the fields of spectroscopy, spectrophotometry, and chemometrics. In particular, the present invention relates to a method of building instrument variation tolerance into calibration algorithms for spectroscopic devices for chemical composition analysis with spectroscopic methods. The method of the present invention is particularly suitable for blood glucose, cholesterol and other chemical components prediction based on near-infrared spectrophotometry measurements.

BACKGROUND OF THE INVENTION

Spectroscopy is a well established method, which has extremely wide applications for chemical analysis of plasma, gases, liquids and solids practically in all field of modern science and technology as well in everyday life including food production, food processing, healthcare and medicine. The role of spectroscopy is to identify and to perform quantitative analysis of chemical composition of various bodies and substances or to recognize and measure concentration one or more selected chemical components (analytes) in the bodies and substances. One of such applications is a non-invasive measurement of different substances like glucose, cholesterol water, fat, protein, hemoglobin, melanin and other in human body, therefore a non-invasive glucose concentration measurement has been selected here as an illustrative example only and cannot be considered as an exclusive area of patent application.

Biotechnological analysis and examination are often based on the measurement of various chemical analytes in the composition of a biological matrix such as blood, interstitial fluid, or living tissue. Such measurements may be used to evaluate a patient's state of health and to determine what, if any, treatment is necessary. For example, the frequent monitoring of blood glucose levels in diabetic persons with glucometers is often necessary to allow such persons to manage the diabetes mellitus disease, by taking insulin injections or oral drugs to lower blood glucose when required. Intensive treatment based on frequent blood glucose measurements can significantly reduce the incidence of blindness, kidney loss, and other complications associated with diabetes.

Most home-based glucose measurement systems require the patient to invasively collect a blood sample, by pricking his or her finger, placing the sample on an appropriate test strip, and then testing the sample in an optical glucometer. For millions of diabetics around the world, the use of lancets or other sharp instruments to draw blood for monitoring their insulin levels is a painful process, and one that often builds up calluses on fingers, making the collection of blood even more difficult. This invasive procedure may be especially difficult to perform on children and therefore particularly trying on parents. Furthermore, the test strips required for each blood sample are generally not reusable, and when multiple measurements are taken each day, amount to significant costs from the patient's point of view. Thus, despite the fact that a large number of diabetics should take several measurements throughout each day (for some individuals, physicians recommend testing glucose levels from 4 to 7 times daily), due to the pain, cost, and inconvenience involved, many diabetics do not monitor their glucose levels frequently enough. A non-invasive means of measuring blood glucose levels is needed to eliminate the pain and risk of infection associated with drawing blood and thus increase the likelihood that diabetics will perform the recommended number of measurements.

For example, spectroscopy of samples containing molecules of various chemical substances is based on the analysis of how incident radiation interacts with the vibrational and rotational states of molecules, which are of analytical interest. Spectroscopic measurement techniques have gained increased popularity because of the ability to provide fast and non-invasive measurements of concentrations of different chemicals or analytes. For the reasons indicated above, this is particularly desirable for home based glucometers. Spectrophotometry is a type of spectroscopy commonly used to quantitatively measure concentrations of analytes based on spectral energy distribution in the absorption spectrum of a sample solution or medium. In spectrophotometry, the spectral power (or energy) distribution is typically analyzed within a selected part of a range of the ultraviolet, visible, or infrared spectra.

For example, near-infrared radiation (NIR) is electromagnetic radiation having a wavelength of between about 0.75 and 2.5 micrometers (i.e. from 120 to 400 THz). Near-infrared spectrophotometry generally uses instruments, which spatially disperse radiation of different wavelengths within this range, and whose spectral power density (or integrated over certain time period spectral energy density) is measured with a suitable radiation detector. The NIR spectrophotometry is increasingly being used to measure in vivo analytes such as glucose, fructose, glycerol, and ethanol.

Non-invasive, spectrophotometric measurement of glucose in human beings is performed by illumination of the selected part of human body with radiation of a known spectral composition and detecting changes in the spectral composition of the radiation interacting with (affected by) the selected body part or sample, in general. Following the Beer's law, most often these changes are expressed in the form of a function which presents a negative logarithm of the ratio of spectral power (or energy) densities of radiation flux affected by the sample to that of incident. Usually this function is referred to as absorbance. For non-absorbing samples, in absence of losses other than radiation absorption in the sample, this function is a constant equal to zero. If absorption of radiation in the sample is spectrally dependent, this function takes different values for different wavelengths (or frequencies) of the radiation and is usually called a spectral absorption (or absorbance) of the sample. Practically all known substances demonstrate absorption of electromagnetic radiation in certain spectral ranges, hence they modify spectral composition of light affected. The relative changes in spectral composition of radiation, caused by different molecules create different patterns spectral absorption pattern, specific for molecules. Therefore, recognition of this pattern can be used for identification of molecules creating the pattern. This is relatively easy when the pattern is created by a single or a very small number of sorts of molecules, with distinctively different absorption spectra. The problem becomes more complex when either the sample contains a large number of sorts of molecules or their spectra are very similar. In particular, the absorbance of the incident radiation by human body is due to presence of the various chemical components within that body as: water, fat, protein, hemoglobin, melanin, glucose and many other components. One difficulty with glucose measurement using spectral analysis, is the spectral overlap between glucose and other chemicals found in blood, often in much greater quantities than glucose. In addition, the thickness, color, and structure of the skin, bones, and blood through which the incident radiation passes affects the spectral changes in light interaction (transmitted, reflected or absorbed. Furthermore, the concentration of analytes can vary with changes in activity level, diet, hormone fluctuations, and other factors. Glucose concentration measurements are also particularly susceptible to variations in physical and chemical conditions including temperature, pressure, humidity, and skin hydration. As a result, to perform a reliable non-invasive glucose prediction, NIR spectral measurements should be performed through a vascular equilibrated region of the body, and a NIR glucose spectrophotometer must be carefully designed so that the quality of raw spectral information from an NIR glucometer is high. See generally Waynant and Chenault, "Overview of Non-Invasive Optical Glucose Monitoring Techniques", *IEEE LEOS Newsletter*, vol. 12, no. 2 (April 1998); and Burmeister and Arnold, "Spectroscopic Considerations for Noninvasive Blood Glucose Measurements with Near Infrared Spectroscopy", *IEEE LEOS Newsletter*, vol. 12, no. 2 (April 1998).

Near-infrared glucose measurements are generally suitable for tissue depths ranging from about 1 mm to 10 cm, and are often performed through a patient's fingertip, although other areas of the body (for example the web between two fingers, an ear lobe, or the upper lip) can also be used. Sample thickness is an important experimental parameter because a greater thickness increases the amount of absorption and thereby lowers the minimum limits for detection, whereas because less incident radiation successfully traverses through a thicker sample (i.e. without being absorbed) effectively increasing the spectral noise: see Burmeister and Arnold, supra.

Problems related to the non-invasive glucose measurement described above, give a good example of complexity of advanced spectrometric measurements. Application of spectroscopy for chemical analysis becomes particularly difficult when either there is big difference between signals produced by different chemical components, or when the spectra of these components are very similar. Sophisticated data processing and analysis methods, known under common name chemometrics, have been developed to deal with complex situations as described above.

In particular, multivariate correlation techniques such as Partial Least Squares (PLS) are commonly used to develop algorithms for extraction of required information from spectral measurements. In applying this process to non-invasive analyte measurements in humans, spectral measurements are made on the selected body part of volunteers. For each spectral measurement, a reference measurement of the target analyte is made from a drawn blood sample. PLS is used to correlate changes in the analyte value to changes in the spectral measurements. A calibration algorithm is developed from this correlation. It is the standard practice to perform all the above mentioned spectral measurements on a single instrument (often referred to as the master) to obtain the most consistent calibration algorithm.

The application of this solution imposes a few problems however. The first problem is related to variability of the spectra produced by sample. This can be caused either by change of the spectra of the substances existing in the sample due to variation of the sample chemical composition, temperature, humidity or pressure and so on, or as a result of the presence in the sample of chemical components that were not present during calibration measurement. The second problem is related to variation in instrument measurement characteristics. The third one arises when an algorithm developed on one instrument has to be translated to other instrument.

The first problem has been addressed by Haaland (David Haaland; *Synthetic Multivariate Models to Accommodate Unmodeled Interfering Spectral Components during Quantitative Spectral Analysis*; Applied Spectroscopy vol 54, 2000, no2 p 246), who describes incorporating a mathematically derived variation caused by "Unmodeled Interfering Spectral Components" into the calibration algorithm. This method involves identifying the spectrum of "spectral interferents" (in an example given in the above publication this is the spectral change of water spectra caused by temperature variation). This spectrum is synthetically added to the original calibration spectra in a random or designated fashion over the range of variation that might be expected in future samples. An example of temperature variation is used in the samples to show that incorporating the interfering spectra from temperature variation improves the prediction of samples that have temperature variation. This document discloses the benefit of synthetic adding of specific spectral contributions from interfering chemical components, but does not address the issue of changes in spectrum caused by variation of technical characteristics of the instrument, which cannot be presented as an addition to the spectra. These include changes in spectral response of the instrument from measurement to measurement due to thermal and mechanical variations, and differences in wavelength calibration of different instruments where algorithm transfer between instruments is required. In a first order of approximation, in both cases, these changes can lead either to shift of whole spectrum, its contraction or expansion, or both effects together. None of these effects can be mathematically modeled by the addition of an interfering spectral component to the spectrum obtained with some instrument at some moment of time. A similar problem arises when the photometric response of the instrument changes over time. Some of these problems have been partially addressed within the art, but none offer a satisfactory solution of the problem when a large number of instruments, whose characteristics may vary over time and in response to environmental changes, has to be calibrated.

An algorithm (typically a calibration algorithm) developed on the master, as described above, is dependent upon the characteristics of the instrument that is used to develop it. Hence, if the characteristics of the instrument change, the algorithm may produce erroneous results. Transfer of the algorithm to other (slave) instruments that have differences in characteristics such as wavelength or spectral shape is often a difficult problem and the subject of much study. A number of techniques have been developed to translate the measurement results made on a slave instrument to match that of a master instrument. For example, a commonly use method is piecewise direct standardization (PDS; described in Y. Wang, D. J. Weltkamo and B. R. Kowalski; Analytical Chemistry vol. 63, 1991, p. 2750). This method is compared to a method based upon neural networks in Despagne et al. (Frederic Despagne, D. Luc Massart, Martin Jansen and Hansvan Daalen; *Intersite Transfer of Industrial Calibration Models*; Analytica Chimica Acta; vol 406, 2000, p233). A description and example of use of another approach, Shenk's algorithm is described in Bouveresse et al. (E. Bouveresse, D. L. Massart and P Dardenne, *Calibration transfer across near-infrared spectrometric instruments* using Shenk's algorithm: effect of different standardization samples; Analytica Chimica Acta; vol 297, 1994, p. 405). A characteristic, and limitation, of the above techniques is that they require measuring a set of standard samples, which are stable, on the master and each slave instrument. This is time consuming when a large number of slave.instruments are involved. It is also difficult to create a set of standard samples with the long-term stability required by a measurement as sensitive to instrument characteristics as glucose, for example. In addition, the translation algorithm developed is only valid as long as the characteristics of the both master and slave instruments remain as they were when the standardization samples were measured on it. Any subsequent change in instrument characteristics will cause errors in the analyte prediction.

For analytes that account for a minor part of the absorbance, such as glucose, minor changes in instrument characteristics result in large errors in the measurement of the analyte. Wavelength and photometric calibration must be used to make each instrument (slave) look like the master instrument. These calibrations must be extremely accurate for the slave instruments to match the master instrument to a sufficient degree so as to not cause unacceptable errors in analyte measurement. Even after these calibrations, small changes in instrument characteristics on a daily or even hourly basis can cause unacceptable error in analyte measurement. What is needed is a way to make the algorithm more tolerant of changes in instrument characteristics.

There has also been a report on the concept of adding more instrument variation into the algorithm as a way of building some tolerance into calibration algorithms (Durmis Ozdemir, Matt Mosley and Ron Williams; *Hybrid calibration Models: An Alternative to Calibration Transfer*; Applied Spectroscopy, vol 52, 1998, p. 599). Ozdemir et al. describes combining spectra measured on two instruments and show that the analytes predictions on the slave is better with an algorithm developed using spectra from both instruments than it is with an algorithm developed using only the spectra measured on the slave. This indicates that incorporating variation into the calibration algorithm could make it more tolerant of similar variations in the instruments when it is used for subsequent measurement. However, this method only includes variations between instruments that happen to occur in the two, or more, instruments that are being measured and only at the time of measurement.

As it follows from the above, there still exists a need for a method allowing incorporation of the instrument variability into calibration algorithm of spectral instrument.

The method as described herein consists in incorporation of wavelength variability of instrument calibration using either multiple instrument data collection for algorithm development or by incorporation of the synthetic instrument variability.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to a method of building instrument variation tolerance into calibration algorithms for spectroscopic devices for chemical composition analysis with spectroscopic methods. The method of the present invention is particularly suitable for blood glucose, cholesterol and other chemical components prediction based on near-infrared spectrophotometry measurements.

The present inventors have determined that partial least squares analysis (PLS) is able to identify patterns of change in a continuous measurement of spectra in a defined range.

Past experience has indicated how changes in spectra caused by scattering, temperature changes, and absorbance offsets due to differences in the interface to the subject are incorporated into an algorithm using the PLS technique. These changes have only a minor impact on the analyte value reported. While these features have been known, surprisingly, the present inventors have found that PLS can also accommodate changes in instrument characteristics, such as wavelength shift, if these changes follow a pattern and are incorporated into the algorithm.

Accordingly, in its broad aspect the present invention provides a method of taking into account the variability of spectral instruments through incorporation of variation expected from multiple instruments into an algorithm.

In an aspect of the present invention, the method comprises:
i) developing a calibration algorithm on a first instrument;
ii) applying the calibration algorithm to a second instrument;
iii) calibrating the second instrument and adjusting the calibration algorithm to account for differences between the first instrument and the second instrument; and
iv) repeating the step of applying (step ii)) in respect of (n) further instruments to provide an algorithm which may be used on all instruments. In developing such an algorithm, the instruments preferably have characteristics which span the ranges of those characteristics expected in all other instruments of the specified model.

According to another aspect of the present invention, the method comprise developing calibration algorithms on different instruments, combining the data collected from the calibrations and incorporating any variations mathematically into the algorithm.

According to yet another embodiment, the method comprises:
i) developing a calibration algorithm on a first instrument;
ii) applying the calibration algorithm to a second instrument;
iii) calibrating the second instrument and adjusting the calibration algorithm to account for differences between the first instrument and the second instrument;
iv) repeating the step of applying (step ii)) in respect of (n) further instruments to provide a first master algorithm;
v) developing one or more of the calibration algorithms on different instruments,
vi) combining the data collected from the one or more calibration algorithms and incorporating any variations mathematically into a second master algorithm; and
vii) combining the first and the second master algorithms to provide a final master algorithm, wherein in developing the final master algorithm, the instruments preferably have characteristics which span the ranges of those characteristics expected in all other instruments of a specified model.

Since the methods of the invention accommodate changes that follow a recognizable pattern, they can be used with instrument configurations that measure continuous spectra. These configurations often exhibit causes for instrument variance that result in patterned changes.

Stated differently these changes can be incorporated into an algorithm in at least 3 ways:

1. Develop the algorithm on multiple instruments either real or virtual, created by mathematical modification of readings obtained with real instruments to incorporate possible spectral and photometric variations of instrument response. The instrument characteristics must span the ranges of those characteristics expected in all other instruments of the specified model;

2. Incorporate the variations mathematically after calibration data has been collected. Again the variations incorporated must span the ranges of those characteristics expected in all instruments of the specified model; or 3. A combination of the above two approaches.

A clear benefit of including multiple instruments in the collection of calibration data is that the resulting algorithm could accommodate variations in characteristics beyond the targeted ones, such as those that affect the spectral shape of the absorbance curve in a specific pattern.

This summary of the invention does not necessarily describe all necessary features of the invention but that the invention may also reside in a sub-combination of the described features.

Other features and advantages of the present invention will become apparent from the following detailed description. It should he understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

The present invention relates to a method of building instrument variation tolerance into calibration algorithms for spectroscopic devices for chemical composition analysis with spectroscopic methods. The method of the present invention is particularly suitable for blood glucose, cholesterol and other chemical components prediction based on near-infrared spectrophotometry measurements.

The following description is of a preferred embodiment by way of example only and without limitation to the combination of features necessary for carrying the invention into effect.

The present inventors have determined that partial least squares analysis (PLS) is able to identify patterns of change in a continuous measurement of spectra in a defined range.

As used herein "concentration" or "concentration level" means the amount or quantity of a constituent in a solution whether the solution is in vitro or in vivo.

As used herein, "constituent" means any substance, or any analyte found in any sample including but not limiting to a tissue and includes but not limited to carbohydrates such as for example glucose, bilirubin, a protein, for example albumin or hemoglobin.

As used herein "sample" means any substance in a form of plasma, gas, liquid or solid, consisting more than one chemical component, whose chemical composition is to be determined. Preferably the chemical composition is determined using spectroscopic methods in any spectral range where spectroscopic methods are applied.

As used herein, "tissue" means any tissue of the body of a subject including for example, blood, extracellular spaces, and can mean the entire composition of a body part such as a finger or ear lobe.

As used herein "subject" means any member of the animal kingdom including, preferably, humans.

The present invention can be used with any spectrophotometer, including but not limiting to those working in NIR, the system having a light source which is projected through the item to be examined, a sample interface mechanism, a spectrometer to separate the light into its component wavelengths, a detector, amplification electronics and a computer. By measuring the loss (absorption), between the source and the detector and applying appropriate chemometric (mathematical) techniques, it is possible to non-invasively determine the chemicals being examined since different chemicals absorb different amounts of light.

Such a spectrophotometric device and method are described in detail in U.S. Pat. No. 5,361,758 (which is incorporated herein by reference). While the present description relates primarily to glucose measurement, one of the major fields of application for NIR measurement at present, it will be understood that the principles of the present invention equivalently apply to other analytes and chemical components measured invasively or non-invasively, using various spectroscopic techniques.

To utilize the NIR spectrum for glucose measurement, it is necessary to use a spectrometer which has wide dynamic range, a high signal to noise ratio, and exhibits low scattering losses. The output from the spectrometer is used to generate spectra with high precision both in absorbance and wavelength. Significant glucose absorption bands are centered about wavelengths of 1.67, 2.13, , 2.27, and 2.33 micrometers (as discussed in Small and Arnold, "Data handling Issues for Near-Infrared Glucose Measurements", supra). To be able to use NIR to measure a particular compound/ analyte, chemometric mathematical analysis is applied to the measured spectrum. The mathematical analysis techniques are carried out by a computer equipped with advanced software capable of interpreting the resulting complex spectra.

To calibrate a spectrophotometer in the normal manner, the instrument response associated with the compound or analyte of interest must first be measured on a relatively large number of samples. These measurements are then compared to measurements made in a more accurate manner. From these comparisons an algorithm is developed that characterizes the compound or analyte to be measured. As was stated earlier, performance by an algorithm generated in this way will be degraded if a) new samples are measured on a slave instrument which measures at wavelengths slightly different from the master instrument, or b) the wavelengths of the master instrument shift between the measurement of calibration samples and measurement of prediction samples.

According to the present invention, to add tolerance to wavelength shifts, new calibration spectra of the samples are created. To create a new spectrum of the sample, the wavelengths of the spectrum of the sample are shifted by a fixed pattern and by a specified amount. The reference analyte (for example but not limited to glucose) value from the original sample is associated with the new sample. Additional new spectra of the samples are created in a like fashion by shifting the wavelengths of additional samples from the original calibration set by the same specified amount. Next the specified amount of the shift is changed to a new level, in a discrete step or by a random number, and additional spectra of the samples are created by shifting the wavelengths of some of the original calibration spectra by this new amount. This process is repeated until the amount of the shift covers the shift that is expected in future instruments.

The pattern of shift can be any pattern that would be expected to occur in the spectrometers. Typical kinds of shifts that occur in spectrometers would include a uniform shift, where the wavelengths for all measurement points shift by the same amount for all points, and a shift that is wavelength dependent. In this second (wavelength dependent) shift, the wavelengths of measurement points shift by a different amount dependent on position of the measurement point on wavelength axis. These and other kinds of shift can be incorporated using the method.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1

Simulator Validation

A series of studies has been initiated using a computer modeling program that simulates each aspect of measuring glucose on patients. The simulator models variations in absorbance of the fingers of multiple patients from effects of analyte combinations, tissue characteristics and finger placement as well as instrument characteristics. It also models the process on the generation of a calibration algorithm and prediction using that calibration algorithm on data that is independent from that used to generate the calibration.

The initial study modeled the effect of a constant shift of all wavelengths in a system that measures 256 wavelengths in a contiguous manner. By a uniform shift is meant that all wavelengths shift the same amount in the same direction. This is one type of change that could be expected in a spectrometer. The error in glucose prediction resulting from various levels of shift was identified. The first lines of Table 1 show an example of the effect of various amounts of wavelength shift on glucose error using the presently accepted method of generating algorithms. These results show that the algorithm is extremely sensitive to wavelength shift. For example from table 1, a shift of only 0.05 nm, not a large variation for even the best spectrometers, causes a six-fold increase in the glucose error.

TABLE 1

Effect of wavelength shift using the present method of generating calibration algorithms(standard) and the new method with 5 wavelength shifts incorporated into the algorithm.

| | Standard Error of Prediction for Glucose vs Wavelength Shift Amount of shift | | | | | | |
|---|---|---|---|---|---|---|---|
| Algorithm type | 0 | 0.001 nm | 0.005 nm | 0.01 nm | 0.02 nm | 0.05 nm | 0.1 nm |
| Standard Method | | | | | | | |
| Error | 2.07 | 2.08 | 2.54 | 3.64 | 6.38 | 15.36 | 30.65 |
| % increase | | 1 | 23 | 76 | 209 | 644 | 1384 |
| New method | | | | | | | |
| Error | 2.35 | 2.35 | 2.35 | 2.36 | 2.37 | 2.42 | 2.57 |
| % increase | | 0 | 0 | 0 | 1 | 3 | 10 |

The simulator (see above) was then operated to incorporate seven groups of new sample spectra where the spectra for each group had been shifted by various amounts from 0 to 0.1 nm as described earlier. The results for this version of algorithm are shown on the bottom lines of Table 1. This shows the dramatic improvement that is made to the robustness of the algorithm.

The results also point out a potential negative impact of this approach. Incorporating wavelength variance into the algorithm increases the error in the case where there is no wavelength shift in the slave instrument(from 2.07 to 2.35). However this negative impact is small compared to the dramatic gains achieved under normal real life conditions where there is a change in instrument characteristics.

Example 2

Another example shows simulator modeling of a system with two wavelength regions. The first contains 256 measurement points as in example above and 33 measurement points in spectral range with longer wavelengths. The wavelengths in the second region are shifted by a uniform amount, but those in the first region stay stable. Using the new method, seven levels of uniform shift has been added to the wavelengths in the second region to a maximum of 0.1 mn.

TABLE 2

Glucose error vs uniform wavelength shift for a system with two wavelength regions

| | Standard Error of Prediction for Glucose vs Wavelength Shift Amount of shift | | | | | |
|---|---|---|---|---|---|---|
| Algorithm type | 0 | 0.005 | 0.01 | 0.05 | 0.1 | 0.2 |
| Standard method | | | | | | |
| Glucose error | 0.61 | 1.39 | 2.60 | 12.74 | 25.46 | 50.87 |
| % increase | | 127 | 325 | 1980 | 4058 | 8208 |
| New method | | | | | | |
| Glucose error | 1.16 | 1.16 | 1.16 | 1.17 | 1.23 | 1.41 |
| % increase | | 0 | −1 | 1 | 5 | 22 |

This example show that using the standard method of generating algorithms, a system of this type is very sensitive to shifts in one part of the spectrum, but the method of this invention reduces this sensitivity dramatically. It also demonstrates that when wavelength shifts occur in the samples in the prediction set that are beyond that added to the calibration set (0.2 nm in this example), the system becomes more sensitive to shift.

Example 3

A further example demonstrates that this method can be used to increase tolerance for wavelength shifts of other patterns. In a system with two wavelength regions as in example 2, wavelengths in the second region are shifted an amount proportional to its position. The first point is not shifted, while the last point is shifted by the amount shown in table 3 and the remaining points are shifted by an amount proportional to their position between the ends.

TABLE 3

Glucose error vs a proportional wavelength shift for a system with two wavelength regions

| | Standard Error of Prediction for Glucose vs Wavelength Shift Amount of shift | | | | | |
|---|---|---|---|---|---|---|
| Algorithm type | 0 | 0.005 | 0.01 | 0.05 | 0.1 | 0.2 |
| Standard method | | | | | | |
| Glucose error | 0.61 | 1.24 | 2.27 | 11.01 | 22.09 | 44.15 |
| % increase | | 103 | 271 | 1697 | 3508 | 7111 |
| New method | | | | | | |
| Glucose error | 1.03 | 1.03 | 1.03 | 1.04 | 1.07 | 1.17 |
| % increase | | 0 | 0 | 0 | 3 | 13 |

This example demonstrates the ability of an algorithm developed using the methods in this invention to increase tolerance to wavelength shifts of various patterns.

Example 4
Human Data Measured On Instruments

A calibration evaluation was performed on data previously measured on 4 human volunteers. The data set consists of 5 days of measurements on each of the 4 patients. Each day consisted of 16 pairs of spectral measurements; each pair matched to a reference glucose measurement. The reference measurement was on whole blood fray a finger stick measured on a Yellow Springs Glucose instrument. Spectral data was taken on 3 different instruments. The wavelengths of the 3 instruments were matched to the best of our ability to measure their wavelengths. Photometric correction was used to match the spectral shape of absorbance measurements of all 3 instruments. These corrections normalize to a reasonable degree the two characteristics that have the most impact on glucose accuracy.

In the first instance, calibration was performed using the presently accepted method. A calibration algorithm was developed on one instrument(referred to as A) using the first 3 days of data. That algorithm was used to predict glucose based upon spectral data measured on instrument A during the last 2 days. The same algorithm was used to predict glucose based upon spectral data measured on two additional instruments (B and C) on the same patients during the last 2 days. Results for this calibration are shown in table 2.

TABLE 2

Glucose error in glucose predictions from multiple instruments using conventional algorithm development techniques.

| | Standard Error of Prediction (SEP) mmol | | |
|---|---|---|---|
| | Instr A | Instr B | Instr C |
| Day 4 | 1.39 | 30.03 | 51.67 |
| Day 5 | 2.77 | 30.62 | 52.86 |

These results show the glucose error resulting from predicting on the same instrument that was used to generate an algorithm(A). The results for instruments B and C show the large increases in error that can occur from relatively small changes in instrument characteristics.

Using the same data, calibration was performed using the method of the invention. Data measured on the first three days on all three instruments was used to generate the algorithm. Predictions of glucose were made using that algorithm based upon spectral data measured on all 3 instruments on the last 2 days as before. The results are shown in table 3.

TABLE 3

Glucose error in glucose predictions from multiple instruments using the new algorithm development technique.

| | Standard Error of prediction (SEP) mmol | | |
|---|---|---|---|
| | Instr A | Instr B | Instr C |
| Day 4 | 1.47 | 2.40 | 2.52 |
| Day 5 | 2.92 | 3.32 | 3.04 |

The theoretical results were verified experimentally applying the same method to measurement obtained with three different instruments.

The results have demonstrated the dramatic improvement in glucose prediction accuracy achieved by combining measurements from multiple spectral instruments in the calibration. While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A method of generating a calibration algorithm adaptable to instrument-specific variations in assigned wavelength, comprising:

measuring a spectral response for each one of a set of calibration samples, each measured spectral response comprising at least one measurement element, each measurement element having an assigned wavelength;

shifting the assigned wavelength of at least one of said at least one measurement element of each measured spectral response by at least one of a random amount, a uniform amount, and a variable amount, that is dependent on the magnitude of the assigned wavelength, wherein at least one modified spectral response, that differs in the amount of shifting, is generated for each of said samples; and using a multivariate analysis method to generate said calibration algorithm from the measured spectral responses and the modified spectral responses of said samples.

2. The method of claim 1, wherein the spectral response for each of the calibration samples is measured on at least two spectral instruments, wherein at least two modified spectral responses are generated from each of the spectral responses measured on said at least two spectral instruments.

* * * * *